United States Patent [19]

Heggs et al.

[11] Patent Number: 4,905,697

[45] Date of Patent: Mar. 6, 1990

[54] TEMPERATURE-CONTROLLED CARDIAC PACEMAKER RESPONSIVE TO BODY MOTION

[75] Inventors: Kevin S. Heggs, Monroeville; William L. Johnson, Kittanning; Donald A. Stevens, Spring Church, all of Pa.

[73] Assignee: Cook Pacemaker Corporation, Leechburg, Pa.

[21] Appl. No.: 310,852

[22] Filed: Feb. 14, 1989

[51] Int. Cl.$^4$ .............................................. A61N 1/36
[52] U.S. Cl. ......................... 128/419 PG; 128/419 P
[58] Field of Search ..................... 128/419 P, 419 PG

[56] References Cited

U.S. PATENT DOCUMENTS

| | | | |
|---|---|---|---|
| 4,140,132 | 2/1979 | Dahl | 128/419 PG |
| 4,428,378 | 1/1984 | Anderson et al. | 128/419 PG |
| 4,436,092 | 3/1984 | Cook et al. | 128/419 PG |
| 4,543,954 | 10/1985 | Cook et al. | 128/419 PG |
| 4,726,383 | 2/1988 | Cook et al. | 128/786 |
| 4,782,836 | 11/1988 | Alt | 128/419 PG |
| 4,803,987 | 2/1989 | Calfee et al. | 128/419 P |

OTHER PUBLICATIONS

Alt et al., "A New Rate-Modulated Pacemaker System Optimized by Combination of Two Sensors," *PACE*, vol. II, No. 8, Aug. 1988, pp. 1119–1129.
Cook Pacemaker Corp., "Sensor Model Kelvin TM 500 Pulse Generator Physician's Manual," Aug. 30, 1987, p. i–59.

*Primary Examiner*—Lee S. Cohen
*Assistant Examiner*—Scott Getzow
*Attorney, Agent, or Firm*—Richard J. Godlewski

[57] ABSTRACT

Method and appartaus are disclosed for stimulating the heart with a pacemaker in response to a nonambient temperature of a body, which is sensed, for example, in the right ventricle of the heart. The pacemaker stimulates the heart at one of at least three different nominal rates which have been selected by the physician for the various activity levels of the patient. When the heart is stimulated at an interim rate for mild or brief exercise conditions, the activity level of the patient is sensed using a motion sensor. A control circuit terminates a predetermined time period selected for the pacemaker to stimulate at the interim rate when the sensed level is less than a predetermined activity level. The stimulation rate of the heart is controlled by the nonambient body temperature sensed in the right ventricle of the heart, but the sensed motion or activity level of the patient is used to terminate the interim time period when the sensed activity level of the patient does not correspond to the level of activity intended for the selected stimulation rate.

21 Claims, 2 Drawing Sheets

TEMPERATURE-CONTROLLED CARDIAC PACEMAKER RESPONSIVE TO BODY MOTION

TECHNICAL FIELD

This invention relates to cardiac pacemakers and particularly to a cardiac pacemaker in which the stimulation rate of the heart within a body is adaptively regulated according to the blood temperature of the body.

BACKGROUND OF THE INVENTION

The human body is equipped to adapt to the increased need for cardiac output during exercise. If the heart is functioning properly, the nervous system increases the heart rate and reduces peripheral resistance in response to exercise. However, a large, increasing population of patients have pacemakers to compensate for various heart conduction disorders. With rate adaptive and exercise-responsive cardiac pacemakers being developed, the pacemaker has not only become a life sustaining device for a significant number of people with cardiac conduction problems, but it has also become a device for improving the quality of life for these patients to lead a more normal existence.

Several physiological measurements have been utilized to indicate pacing rates during exercise. These physiological parameters include pH, QT interval, respiratory rate, body motion, and the venous blood temperature in the right ventricle of the heart. Blood temperature is a good physiological indicator for several reasons. During exercise, muscles generate considerable heat, causing an increase in the temperature of venous blood. Factors other than exercise such as emotional anxiety also cause an increase in blood temperature. Even the anticipation of activity causes a brief decrease in the temperature of mixed venous blood.

A typical blood temperature response to activity or stress from a baseline temperature initially includes a sudden and brief decrease in temperature, which is caused by peripheral vasodilation at the onset or anticipation of exercise. This temperature drop is followed by a rise in temperature or by a brief leveling off period and then a rise in temperature. If the activity is brief, the temperature will slowly return toward the baseline temperature. If the activity or exercise continues, the temperature rises more rapidly and continues to rise until the activity ceases. After exercise ceases, the temperature returns toward the baseline.

Temperature profiles vary among patients. The magnitude of each component of the temperature response varies with the individual patient and the level of activity. Some patients tend to exhibit a pronounced drop, while others exhibit no drop or only a slight temperature drop. More strenuous activities cause a faster rise in temperature. Also, repeated activity during a short time period tends to reduce the magnitude of the drop by decreasing the temperature difference between central and peripheral circulation.

One temperature-based, rate-adaptive pacemaker is the KELVIN ™ 500 pacemaker manufactured by Cook Pacemaker Corporation of Leechburg, Pa. This pacemaker includes a pacing algorithm that controls the stimulation rate of a pulse generator between programmable lower, interim, and upper stimulation rates; which are normally associated with resting, brief exercise, and continued exercise conditions, respectively. Sensitivity to temperature changes and the speed of stimulation rate changes are separately programmable. This pulse generator recognizes the initial decrease in temperature at the onset of activity and increases the stimulation rate to the programmed interim rate appropriate for short duration activities. This provides an early increase in the stimulation rate, while limiting further rate increases until sustained activity is confirmed by a temperature rise. This is also a safety feature which limits the stimulation rate to the programmed interim rate until a continued temperature rise is confirmed.

The pulse generator stimulates the heart at the interim rate for a programmed interim time period if a sufficient temperature rise to indicate continued activity does not occur. Basically, this interim time period allows for stimulation at the interim rate during short bursts of activity, which are generally unaccompanied by a sufficient temperature rise for stimulation at the upper rate. When the activity is brief and does not cause a sufficient temperature rise, the stimulation rate of the generator returns to the programmed lower rate after the programmed interim time period has elapsed or terminated. When sustained exercise is confirmed by a sufficient positive temperature rise over time, the stimulation rate of the generator is increased to the programed upper rate. When exercise ceases, the temperature returns toward the baseline temperature, and the stimulation rate returns to the lower rate. When the post-exercise temperature decreases rapidly, the stimulation rate may be maintained at the interim rate for the interim time period before returning to the lower rate, which provides additional cardiac output.

The predetermined interim time period is programmable presently from 2-12 minutes in 2 minute increments with an interim time period of six minutes being satisfactory for most patients. However, even with an interim time period of six minutes, patients have complained of the elevated stimulation rate for the entire interim time period after experiencing mild or brief exercise such as sitting or standing up from a prone position. Since the interim time period is selected to meet the overall needs of the patient, it would be desirable to modify the interim time period based on the real time exercise level of the patient.

SUMMARY OF THE INVENTION

The foregoing problems are solved and a technical advance is achieved in an illustrative temperature-controlled, cardiac pacemaker for stimulating a heart at a predetermined rate for a given activity or motion level and including a motion sensor for sensing a motion of a patient's body and terminating the predetermined time period established for the predetermined stimulation rate when the motion sensed during the time period is less than a predetermined level. The illustrative temperature-controlled cardiac pacemaker includes a temperature sensor for sensing a nonambient temperature of the patient's body. Illustratively, the temperature sensor is placed in the right ventricle of the patient's heart, the temperature therein indicating the relative activity level of the patient. The pacemaker also includes a control circuit for controlling the stimulation rate of the heart according to an algorithm which represents the relationship between the nonambient temperature and the stimulation rate. Responsive to the nonambient temperature, the control circuit produces a rate control signal indicative of a predetermined stimulation rate for a predetermined time period when the relationship reaches a predetermined threshold. An initial decrease in the nonambient temperature typically indicates the onset of activity or exercise. As a result, the pacemaker elevates the stimulation rate from a resting to an interim rate which provides sufficient cardiac output to meet the demands of the elevated activity level. Advantageously, the pacemaker further includes a motion sensor for sensing the motion of the patient's body, the control circuit being further responsive to the sensed motion for terminating the predetermined time period when the motion during the time period is less than a predetermined level. Illustratively, this predetermined motion level is greater than that of a short duration activity such as standing or sitting up from a prone position. This advantageously causes the stimulation rate to be returned to the resting rate upon sensing the lack of continued exercise.

The pacemaker further comprises a pulse generator for stimulating the heart at a predetermined stimulation rate in response to the rate control signal indicative thereof.

The control circuit of the pacemaker includes an algorithm circuit for implementing the algorithm and a rate control circuit for producing rate control signals indicative of the lower, interim, and upper stimulation rates.

The algorithm circuit includes a multistate control circuit for indicating a plurality of stimulation rates such as the lower, interim, and upper stimulation rates. Included in this multistate control circuit are first and second state circuits for indicating first and second predetermined stimulation rates, respectively. Illustratively, the first state circuit indicates an interim stimulation rate for mild or brief exercise or activity, whereas the second state circuit indicates a stimulation rate indicative of a resting condition.

Responsive to the indicated stimulation rates, the rate control circuit includes a multiple rate timer for producing rate control signals indicative of the various predetermined stimulation rates.

The algorithm circuit has a plurality of states such as resting, interim, and exercise states and includes, for example, a resting state circuit for transitioning the algorithm circuit to the interim state for indicating an interim stimulation rate for an interim time period when the mathematical relationship represented by the algorithm reaches a predetermined threshold. When in the interim state, the algorithm circuit is responsive to the motion sensor for terminating the predetermined time period. When activity below the predetermined level is sensed, the algorithm circuit is transitioned to the resting state for indicating a resting condition stimulation rate.

The temperature sensor of the cardiac pacemaker includes a thermistor for insertion into the right ventricle of the heart, whereas the motion sensor includes a piezoelectric crystal for sensing body motion.

The method of the present invention involves controlling the stimulation rate of the heart according to the level of muscle activity in the patient's body. The method includes sensing a nonambient temperature indicative of the level of muscular activity in the body and controlling a cardiac pacemaker for stimulating the heart at a predetermined stimulation rate for a predetermined period of time according to an algorithm which relates the nonambient temperature to the stimulation rate of the heart. A departure in the art includes also sensing the motion of the body and advantageously terminating the predetermined time period when the motion of the body during the predetermined time period is below a predetermined motion level. The method further includes controlling the cardiac pacemaker for stimulating the heart at a second predetermined rate when the mathematical relationship of the algorithm is below a threshold.

DETAILED DESCRIPTION

Figure 1:
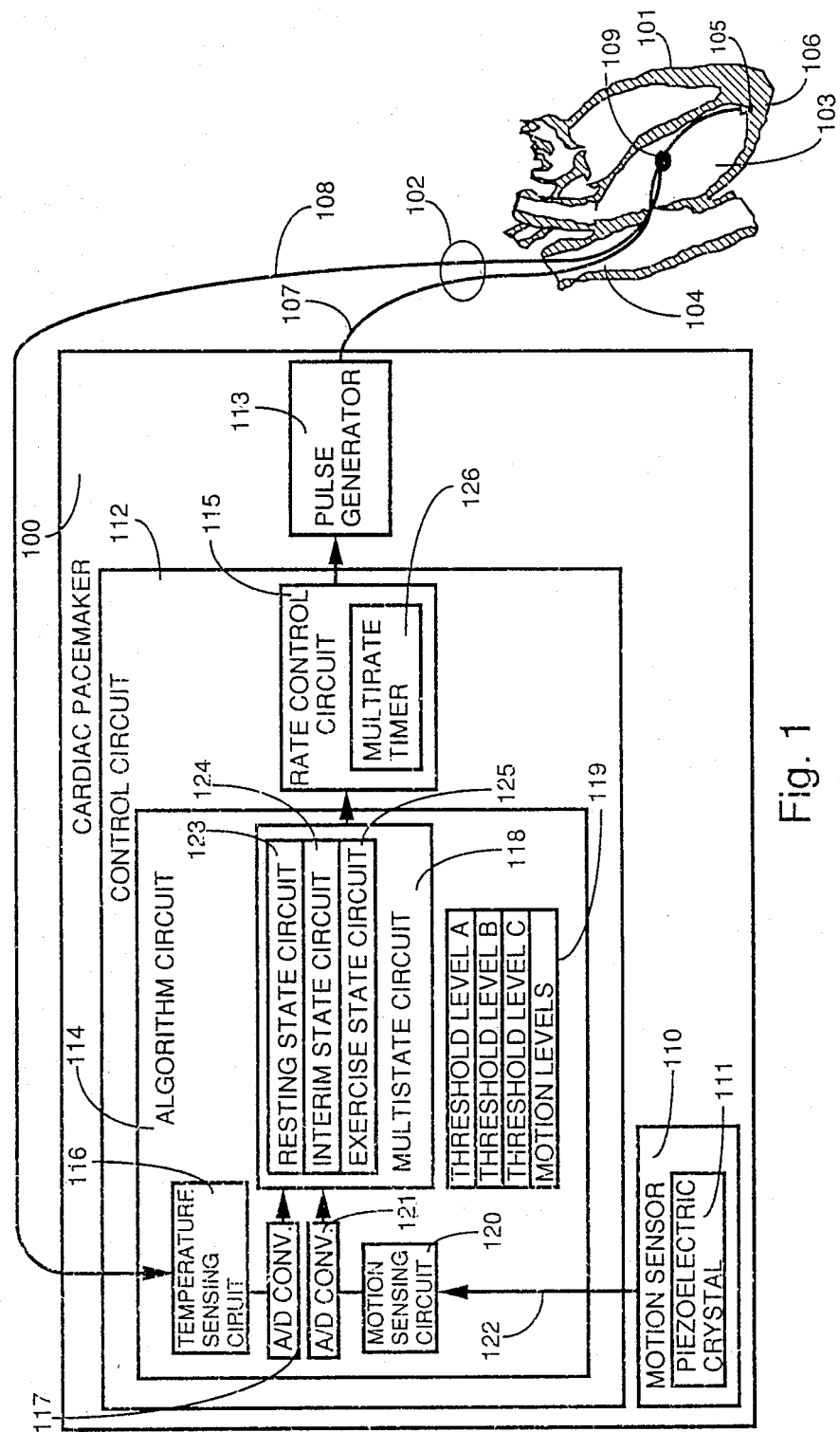
FIG. 1 depicts a block diagram of a cardiac pacemaker of the present invention for stimulating a heart at a predetermined stimulation rate for a given period of time.

Depicted in FIG. 1 is a block diagram of an illustrative temperature-controlled, rate adaptive cardiac pacemaker 100 for stimulating heart 101 of a patient (not shown) via heart pacemaker lead 102. Heart lead 102 is surgically implanted subcutaneously in a well-known manner in the right ventricle 103 of the heart via the superior vena cava 104. At the distal end, the heart lead includes pacing electrode 105, which is implanted at the apex 106 of the right ventricle. Heart lead 102 also includes an electrical pacing conductor 107 for conducting a stimulating signal from the pacemaker to the pacing electrode and heart. The stimulating signal stimulates the heart at a predetermined stimulation rate determined by the cardiac pacemaker. Also included in heart lead 102 is a pair of electrical conductors 108 for conducting a temperature signal from thermistor 109 that is centrally positioned in the right ventricle 103 of heart 101. Thermistor 109 senses the temperature of the blood contained in the right ventricle 103 of heart 101. Heart lead 102 is commercially available from Cook Pacemaker Corporation and is described in detail in U.S. Pat. No. 4,726,383, issued to Cook et al. and entitled "Exercise-Responsive Cardiac Pacemaker Lead." Reference is made to this patent for a detailed description of the construction and operation of such an illustrative heart lead.

Pacemaker 100 includes a second sensor, motion sensor 110, for sensing the motion of the patient's body. This motion indicates the activity or exercise level of the patient's body. Motion sensor 110 includes a well-known piezoelectric crystal 111 for sensing the motion of the patient's body. Any one of a number of parameters generated by the piezoelectric crystal is used to indicate the activity level of the patient. For example, frequency, voltage, or power developed by the crystal in response to body motion is used singly or in combination to indicate the level of body motion.

The blood temperature sensed by thermistor 109 controls the stimulation rate of the heart per an algorithm which represents a mathematical relationship between a nonambient blood temperature and the heart rate of a normal heart. This algorithm is implemented by cardiac pacemaker 100 to control the stimulation rate of the heart. Cardiac pacemaker 100 stimulates the heart at basically three different stimulation rates known as the resting, interim, and exercise rates and incrementally transition from one stimulation rate to another based on the sensed nonambient blood temperature in the heart. One such commercially available temperature-controlled pacemaker is the KELVIN TM 500 pulse generator that is available from Cook Pacemaker Corporation. A detailed description of this temperature-controlled, rate adaptive cardiac pacemaker is described in U.S. Pat. Nos. 4,436,092 and 4,543,954 of Cook et al., entitled "Exercise Responsive Cardiac Pacemaker."

Pacemaker 100 stimulates the heart at the interim rate for a predetermined period of time referred to as the interim time period. During this interim time period, the activity level of the patient's body sensed by motion sensor 110 is compared with a predetermined activity level. When the sensed activity level is less than the predetermined activity level, a control circuit 112 of the pacemaker terminates the interim time period which causes the pacemaker to incrementally change the stimulation rate of the heart to the resting rate.

It has been determined that there exists a relationship between a body's need for increased cardiac output due to exercise and venous blood temperature. Further, because blood entering the right ventricle of the heart is a combination of blood from the upper body via the superior vena cava and from the lower body via the inferior vena cava, the right ventricle is an appropriate location from which is determined the average temperature of blood returning from all of the body's musculature. It is important to note that this temperature will differ from body core temperature and therefore represents a nonambient body temperature. As a result of a number of tests on experimental dogs, the following model equation (1) was derived which closely resembles the relationship between right ventricular venous blood temperature and exercise rate:

$$T_i = a(T_i - 1 - T_0) + bE_i + T_0 \quad (1)$$

In the above equation (1), $T_i$ is the temperature in degrees centigrade at the sample time interval i; $T_i-1$ represents the temperature in degree centigrade at the sample time interval previous to interval i; $T_0$ represents the average right ventricular venous blood temperature during rest; $E_i$ represents the exercise rate of the subject on a treadmill in miles per hour at interval i; a is a constant which represents the controlling temperature coefficient; and b is a constant which represents the controlling exercise coefficient.

Based upon the observed relationship between the heart rate and venous blood temperature in the right ventricle during different levels of exercise, a simple, practical and implemental algorithm was derived to produce a physiological optimal heart rate. Thus, the relationship between venous blood temperature in the right ventricle and heart rate may be described by the following mathematical equation:

$$H_R = A + B(T - T_0) + C \, \text{sign}(dT/dt) \quad (2)$$

In the above equation (2), $H_R$ represents the instantaneous heart rate in beats per minute; A represents the resting heart rate in beats per minute; B represents the slope of the heart rate versus temperature curve during exercise, T represents the smoothed or filtered instantaneous right ventricular temperature in degrees centigrade; $T_0$ is the resting rate ventricular temperature in degrees centigrade; C represents the initial rise in heart rate in beats per minute at the beginning of exercise divided by the slope of the temperature versus time curve during exercise; and dT/dt represents the derivative of temperature with respect to time.

It should be noted that while the above equation was derived from experimental data on test dogs, this data generally agrees with data taken from human subjects and reported in the literature. The observed results are basically similar to the human data except that the slope of the temperature versus time curve in the human suggests an exponitially shaped increase in temperature versus time while the data on test dogs shows a near linear increase in temperature in many cases. This difference is probably because the human species perspires to dissipate excess heat while a dog dissipates heat by panting. Since perspiration is a much more efficient method for heat dissipation than panting, the heat dissipated by perspiration equals the excess heat produced by exercise at a lower temperature than by panting. Hence, the coefficients in the above equation and perhaps the former equation may be slightly different for human subjects.

It should also be understood that other mathematical equations may be derived in order to approximate the observed relationship between venous blood temperature and heart rate, and thus may also be used as control algorithms. Further, the equation (2) described above may be simplified while producing a suboptimal response.

Figure 3:
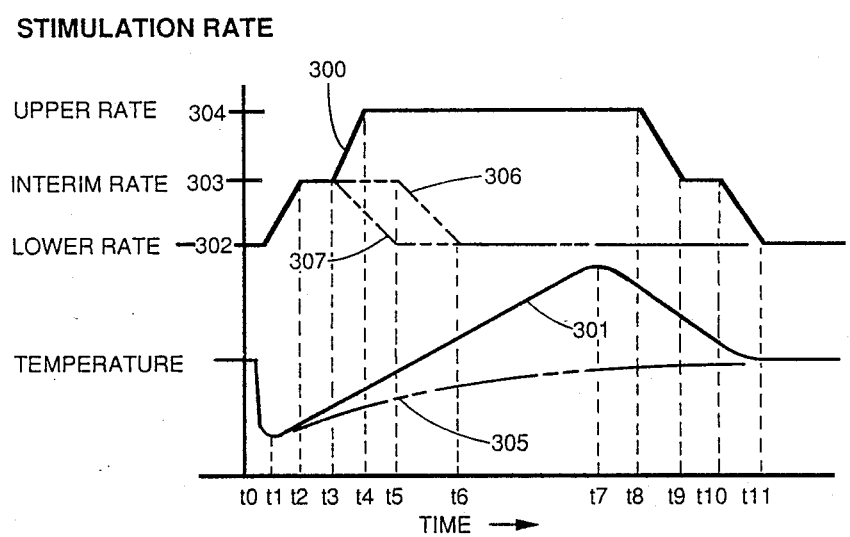

Depicted in FIG. 3 are generalized stimulation rate response 300 and temperature profile 301 both plotted with respect to time. The stimulation rate is allowed to vary between a lower rate 302, an interim rate 303, and an upper rate 304 which are programmed into pacemaker 100, which is depicted in FIG. 1, using well-known telemetry. Lower rate 302 stimulates the heart for a resting condition. Interim rate 303 is for brief or mild activity or exercise, upper rate 304 is for continued activity or exercise.

At the onset of activity at time t0, the temperature drops briefly as shown by profile 301 between times t0 and t1, which causes the stimulation rate to increase from lower rate 302 to interim rate 303 between times t0 and t2. As a fast temperature rise indicates continued activity as shown by profile 301, the stimulation rate increases further to upper rate 304 between times t3 and t4. When a temperature drop is not followed by a sufficient temperature rise as indicated by profile 305 for brief or mild activities, the stimulation rate increases to the interim rate for a predetermined time period as shown by response 306 between times t2 and t5, and then returns to the lower rate between times t5 and t6. When exercise ceases as shown by profile 301 at time t7 followed by a fast temperature decrease, the stimulation rate returns from the exercise rate 304 to lower rate 302 via interim rate 303 between times t8 and t11. The stimulation rate is maintained at the interim rate for the predetermined interim time period between times t9 and t10 before returning to the lower rate. This provides additional stimulation rate support during recovery. When a slower temperature decrease follows a temperature rise, the stimulation rate decreases directly from the upper to the lower rate.

Figure 2:
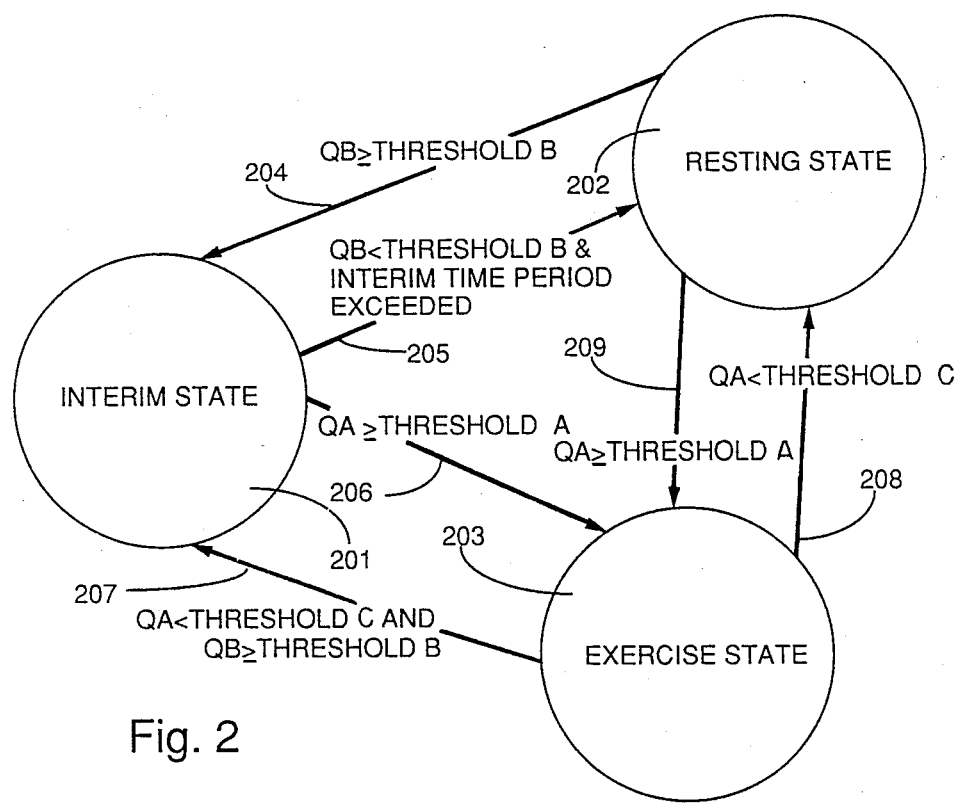
FIG. 2 depicts a state diagram utilized by the pacemaker of FIG. 1 for controlling the stimulation rate of the heart; and FIG. illustrates the stimulation rates of the pacemaker of FIG. 1 and venous blood temperature both as a function of time.

Depicted in FIG. 2 is a state diagram of the algorithm utilized by pacemaker 100 for controlling the stimulation rate of heart 101. The algorithm represents the mathematical relationship between the nonambient temperature of the blood in the right ventricle of the heart and the stimulation rate of the heart. The algorithm incorporates mathematical heart rate equation (2) as applied to the generalized stimulation rate response with the lower, interim, and upper rates and the predetermined interim time period described with respect to FIG. 3. The state diagram as shown includes an interim state 201, a resting state 202, and an exercise state 203. Transition legs 204 and 205 indicate transitions between the interim and resting states 201 and 202. Alongside each leg is a necessary set of conditions for a transition to occur between the resting and interim states.

When in resting state 202, pacemaker 100 stimulates heart 101 at a resting condition stimulation rate. This resting rate is the lower stimulation rate selected for the patient by the physician. In the resting state, the pacemaker is commonly programmed to stimulate the heart at a rate of 70 beats per minute. In the interim state, the pacemaker is commonly programmed to stimulate the heart at 85 beats per minute. In the exercise state 203, pacemaker 100 is commonly set to stimulate the heart at a rate of 110 beats per minute. Again, these three rates are programmable and are established by the physician caring for the patient. Transitions from one stimulation rate to another are performed in incremental steps, the rate of change of these steps with respect to time also being programmable. The transition from one stimulation rate to another occurs when the indicated conditions associated with a transition leg are met. The algorithm utilized by pacemaker 100 also includes a number of parameters, QA and QB, that represent various probabilities of exercise. For example, when the parameter QB is greater than or equal to a threshold level, the pacemaker transitions from resting state 202 to interim state 201 as indicated by transition leg 204. Parameter QB is represented by the following mathematical equation:

$$QB = TauB(dT/dt), \qquad (3)$$

where TauB is a multiplier of the negative derivative of the temperature profile. TauB is a constant which is empirically derived from simulations using exercise temperature data and is set by the physician utilizing the KELVIN SET described in the hereinafter-referenced physician's manual. The KELVIN SET is a physician selectable parameter which represents groups of preselected threshold levels and constants for the pacemaker software. The parameter QB is compared with threshold level B. Threshold level B indicates when the rate of change of temperature with respect to time associated with a temperature drop is sufficient to indicate when a patient begins exercise. When QB exceeds or equals the threshold, the pacemaker changes from the resting state to the interim state for stimulating the heart at the interim stimulation rate for the interim time period.

Transition leg 205 represents the transition from the interim to the resting state when the parameter QB is less than threshold level B and the interim time period has expired or terminated. As indicated in FIG. 3, this typically occurs after time t1. At time t1, blood temperature has reached a minimum and will start to rise. As a result, the rate of change of temperature with respect of time has changed signs. Furthermore, as the blood temperature continues to rise toward the baseline temperature, the interim time period is being timed.

During the interim time period, the level of motion or activity sensed by the motion sensor of the pacemaker circuit is compared with a predetermined activity level. When the activity level is above a predetermined level indicative of exercise requiring the interim heart rate, the interim time period is allowed to continue without interruption as previously described. However, in accordance with this invention, when the activity level of the body is below the predetermined activity level, the interim time period is immediately terminated, and the pacemaker changes state from interim state 201 to resting state 202 as indicated by transition leg 205. As a result, pacemaker 100 changes the stimulation rate from the interim to the resting rate. This condition is depicted in FIG. 3 by temperature profile 305 after time t1 and by phantom stimulation rate response curve 307 between times t3 and t5. As a consequence, the stimulation rate of the patient's heart is decreased from the interim rate to the resting rate without the discomfort of an elevated rate when the patient has completed his brief or mild activity.

Transition legs 206 and 207 represent transitions between the interim and exercise rate states 201 and 203 when the indicated conditions are met. In particular, the pacemaker changes from the interim to the exercise state when parameter QA is greater than or equal to threshold level A. The probability of exercise, QA, is represented by the following mathematical equation:

$$QA = TauA(dT/dt) + DELTAT, \qquad (4)$$

where TauA is a multiplier of the positive derivative of the temperature profile. TauA is a constant which is empirically derived from simulations using, again, exercise temperature data. It is used to scale the relationship between relevant temperature changes as indicated by the rate of change of temperature with respect to time. The constant TauA is set by the physician utilizing the KELVIN SET. DELTAT represents the difference between the present temperature and a resting rate temperature. When the probability of exercise, QA, exceeds or equals threshold level A indicative of continued exercise, the pacemaker changes from the interim to the exercise state and increases the stimulation rate to the predetermined upper rate established by the physician. This is depicted in FIG. 3 times t3 and t4 of the stimulation rate response curve 300. Transition leg 207 represents the transition from the exercise to the interim rate states typically occurring after completion of exercise. This transition is initiated when the probability of exercise QA is less than threshold C and the probability of exercise QB is greater than threshold B. This typically occurs times t8 and t9 as shown in FIG. 3.

Transition legs 208 and 209 represent the conditions under which pacemaker 100 changes state between the exercise and resting states. When the probability of exercise QA is less than a threshold activity level C, the pacemaker transitions from the exercise to the resting state with an accompanying change in the stimulation rate. Additionally, when the probability of exercise QA is greater than or equal to threshold activity level A, the pacemaker transitions directly from the resting to the exercise state. Transitions from the exercise to the interim state followed by the resting states typically occurs when the patient experiences a fast temperature decrease following exercise. This provides additional interim rate stimulation support for the interim time period during recovery. When the patient experiences a more gradual temperature decrease following exercise, the pacemaker will change from the exercise to the resting state as indicated by transition leg 208. A more detailed description of the KELVIN ™ 500 pacemaker along with its' algorithm, features, and programmable parameters are described in the physician's manual provided with the pacemaker from Cook Pacemaker Corporation of Leechburg, Pa., entitled "SENSOR Model KELVIN TM 500 Pulse Generator Physician's Manual."

Returning the reader's attention to FIG. 1, cardiac pacemaker 100 includes control circuit 112 for producing a rate control signal indicative of a predetermined stimulation rate for pulse generator 113. Pulse generator 113 is well-known and is utilized for stimulating the heart at any one of a plurality of predetermined stimulation rates indicated by the rate control signal from control circuit 112. Pulse generator 113 is connected to pacing electrode 105 via electrical conductor 107. Pulse generator 113 produces a signal on conductor 107 for stimulating the heart at the predetermined stimulation rate indicated by the control circuit. Although not shown, the pacemaker of the illustrative embodiment includes a power supply connected to the control and pulse generator circuits for stimulating the heart.

Control circuit 112 includes algorithm circuit 114 and rate control circuit 115. Algorithm circuit comprises temperature sensing circuit 116, analog-to-digital convertor 117, and multistate circuit 118 for responding to the temperature signals received via conductor pair 108 from thermistor 109 and correlating the temperature signal to a heart rate indicated by mathematical equation (2) as previously described. The output of thermistor 109 is connected via conductor pair 108 to the input of temperature sensing circuit 116 which is a preamplifier circuit that linearizes the thermistor output versus temperature over the temperature range encountered by thermistor 109. The resistance across thermistor 109 varies in a known manner with temperature. The output voltage across temperature sensing circuit 116 is an analog representation of the instantaneous right ventricular blood temperature. The output of temperature sensing circuit 116 is connected to the input of analog-to-digital convertor 117. Analog-to-digital convertor 117 converts the analog input voltage from temperature sensing circuit 116 to a multiple bit data word. Digital output of analog-to-digital convertor 117 is sent to multistate circuit 118 which converts the temperature to a heart rate according to the algorithm including the mathematical equations, parameters, and time periods previously described. Multistate circuit 118 comprises a well-known microprocessor and associated program and data memories for storing program instructions and data according to the state diagram previously discussed and depicted in FIG. 2. Threshold levels A-C and predetermined motion levels are stored in a data memory generally designated 119. The microprocessor is programmable by one ordinarily skilled in the art to implement the algorithm representative of the mathematical equations, parameters, and time periods relating the heart rate to the sensed blood temperature and sensed motion as previously described. This relationship is a mathematical relationship which is readily implemented by one ordinarily skilled in the art.

Motion sensor 110 is attached to the casing of the pacemaker in a well-known manner and is connected to the input of motion sensing circuit 112 via conductor 122. The analog signal from the motion sensor linearizes the motion sensor output to an analog signal that represents the range of activity levels experienced by a patient. The output of motion sensing circuit 120 is connected to the input of analog-to-digital convertor 121. Convertor 121 converts analog input voltage from motion sensing circuit 120 to a multiple bit data word. Multistate circuit 118 in response to the data words indicative of the sensed nonambient body temperature and the activity level of the patient implements the signals utilizing the aforementioned algorithms and mathematical equations to indicate a predetermined stimulation rate for rate control circuit 115. Multistate circuit 118 includes resting state circuit 123, interim state circuit 124, and exercise state circuit 125 which are utilized to indicate the interim, resting, and exercise states of algorithm circuit 114 as previously described and depicted in FIG. 2. The output of algorithm circuit 114 is connected to the input of rate control circuit 115. Rate control circuit is a well-known circuit including a well-known multirate timer 126 for producing a rate control signal indicative of predetermined stimulation rate. Thus, when algorithm circuit is in a resting state, rate control circuit produces a rate control signal indicative of the resting stimulation rate which is applied to the input of pulse generator 113. Similarly, when algorithm circuit 114 is either in the interim or exercise states, the rate control circuit produces a rate control signal indicative of the interim or exercise stimulation rates, respectively.

In response to the indicated stimulation rate, pulse generator stimulates the heart at the indicated predetermined stimulation rate.

In summary, cardiac pacemaker 100 stimulates a heart at one of at least three nominal stimulation rates established by the attending physician. Transitions between these stimulation rates are incremental with a rate of change again selected by the physician. When an interim stimulation rate is indicated for brief or mild activity, pacemaker 100 stimulates the heart for an interim time period again as selected by the physician. The activity or motion level of the patient during this period is sensed by the motion sensor and compared with a predetermined level to verify that the interim rate is in fact required by the patient. When the interim rate is not justified by the actual activity level of the patient, the interim time period is terminated, and the stimulation rate of the pacer is returned to the resting rate.

It is to be understood that the above-described method and apparatus for stimulating a heart in response to temperature and activity level measurements is merely an illustrative embodiment of the principles of this invention that other apparatus and method may be devised by those skilled in the art without departing from the spirit and scope of this invention. In particular, the pacemaker may utilize a different state diagram with a different combination of hardware and software to implement the indicated states. Such states may be readily recognized by one skilled in the art as being designed using discrete components or a combination of hardware and software components as illustratively described. Furthermore, a minimum predetermined time period may be established for any of the other stimulation rates and terminated when the motion sensor does not sense an activity level associated with the stimulation rate. Such a period was described for the interim stimulation rate; however, a predetermined period may also be established for the exercise stimulation rate which will default to either the resting or interim rates depending on the temperature sensed. Similarly, an additional resting state may be added for conditions such as sleeping where an even lower stimulation rate would be more appropriate. Sensed activity would also terminate any predetermined time period established for such a stimulation rate.

What is claimed is:

1. A cardiac pacemaker comprising:
    means for sensing a nonambient temperature of a body;
    means for sensing a motion of said body; and
    control means for controlling a stimulation rate of a heart in said body according to an algorithm which represents a relationship between said nonambient temperature and said stimulation rate, said control means being responsive to said nonambient temperature for producing a first rate control signal indicative of a first predetermined stimulation rate when said relationship reaches a predetermined threshold, a predetermined time period being established for the stimulation rate of said heart to occur at said first rate, and further responsive to motion sensed by said motion sensing means for terminating said predetermined time period when said motion during said predetermined time period is less than a predetermined level.

2. The pacemaker of claim 1 further comprising generator means responsive to said first rate control signal for stimulating said heart of said body at said first predetermined stimulation rate.

3. The cardiac pacemaker of claim 1 wherein said control means includes algorithm means for implementing said algorithm.

4. The cardiac pacemaker of claim 3 wherein said control means includes rate control means for producing said first rate control signal indicative of said first predetermined stimulation rate when said algorithm means indicates said first predetermined stimulation rate.

5. The cardiac pacemaker of claim 4 wherein said algorithm means includes means for indicating a second predetermined stimulation rate when said motion during said predetermined time period is less than said predetermined level.

6. The cardiac pacemaker of claim 5 wherein said rate control means includes means for producing a second rate control signal indicative of said second predetermined stimulation rate when said algorithm means indicates said second predetermined stimulation rate.

7. The cardiac pacemaker of claim 3 wherein said control means includes rate control means for producing a second rate control signal indicative of a second predetermined stimulation rate when said algorithm means indicates said second predetermined stimulation rate.

8. The cardiac pacemaker of claim 3 wherein said algorithm means comprises multistate means for producing said first rate control signal and a second rate control signal indicative of a second predetermined stimulation rate.

9. The cardiac pacemaker of claim 8 wherein said algorithm means has a plurality of states and includes second state means for transitioning said algorithm means to a first of said states for indicating said first predetermined stimulation rate when said relationship reaches said predetermined threshold.

10. The cardiac pacemaker of claim 9 wherein said rate control, .means includes means for producing said first rate control signal indicative of said first predetermined stimulation rate when said algorithm means is in said first state.

11. The cardiac pacemaker of claim 10 wherein said algorithm means includes first state means for transitioning said algorithm means to a second state when said motion during said predetermined time period is less than said predetermined level.

12. The cardiac pacemaker of claim 3 wherein said algorithm means has a plurality of states and includes first state means responsive in a first of said states for transitioning said algorithm means to a second of said states for indicating a second predetermined stimulation rate when said motion during said predetermined time period is less than said predetermined level.

13. The cardiac pacemaker of claim 12 wherein said algorithm means includes second state means responsive in said second state for transitioning said algorithm means to said first state for indicating said first predetermined stimulation rate when said relationship reaches said predetermined threshold.

14. The cardiac pacemaker of claim 13 wherein said control means includes rate control means for producing said first and second rate control signals when said algorithm means indicates said first and second predetermined stimulation rates, respectively.

15. The cardiac pacemaker of claim 14 further comprising generator means responsive to said first and second rate control signals for stimulating said heart at said first and second predetermined stimulation rates, respectively.

16. A cardiac pacemaker for controlling a stimulation rate of a heart in a body according to a level of muscular activity in said body, comprising;
    temperature sensor means for sensing a nonambient temperature indicative of said level of muscular activity in said body,
    motion sensor means for sensing a motion of said body, and
    algorithm implementing circuit means for controlling said stimulation rate of said heart according to an algorithm which represents a mathematical relationship between said nonambient temperature and said stimulation rate, said algorithm circuit means for indicating a first predetermined stimulation rate when said mathematical relationship reaches a predetermined threshold, a predetermined time period being established for the stimulation rate of said heart to occur at said first rate, and for further controlling said predetermined time period to be terminated when said motion during said predetermined time period is less than a predetermined level.

17. The cardiac pacemaker of claim 16 further comprising a generator circuit connected to said algorithm circuit means for stimulating said heart at said predetermined stimulation rate.

18. The pacemaker circuit of claim 16 wherein said temperature sensor means includes a thermistor for insertion in the right ventricle of said heart.

19. The pacemaker circuit of claim 16 wherein said motion sensor means includes a piezoelectric crystal.

20. A method of controlling a stimulation rate of a heart in a body according to a level of muscular activity in said body, comprising the steps of:
    sensing a nonambient temperature indicative of said level of muscular activity in said body;
    sensing a motion of said body;
    controlling a cardiac pacemaker for stimulating said heart at a predetermined stimulation rate for a predetermined time period according to an algorithm which relates said nonambient temperature to said stimulation rate of said heart; and terminating said predetermined time period when said motion of said body during said predetermined time period is below a predetermined level.

21. The method of claim 20 further comprising controlling said cardiac pacemaker for stimulating said heart at a second predetermined stimulation rate when a mathematical relationship of said algorithm is below a predetermined threshold.

* * * * *